United States Patent
Eldor

Patent Number: 5,163,901
Date of Patent: Nov. 17, 1992

[54] DEVICE FOR COMBINED SPINAL AND EPIDURAL ANESTHESIA

[76] Inventor: Joseph Eldor, 4 Hanayadot Street, Pisgat Zeev 97536, Jerusalem, Israel

[21] Appl. No.: 716,659

[22] Filed: May 28, 1991

[30] Foreign Application Priority Data

May 28, 1990 [IL] Israel .................................. 94522

[51] Int. Cl.⁵ .............................................. A61M 3/00
[52] U.S. Cl. ...................................... 604/44; 604/158
[58] Field of Search ............... 604/158, 161, 164, 165, 604/166, 167, 264, 44, 43, 272

[56] References Cited

U.S. PATENT DOCUMENTS

| | | | |
|---|---|---|---|
| 4,808,157 | 2/1989 | Coombs | 604/44 |
| 4,958,901 | 9/1990 | Coombs | 604/158 X |

FOREIGN PATENT DOCUMENTS 2124503 2/1984 United Kingdom.

Primary Examiner—John D. Yasko
Attorney, Agent, or Firm—Sandler, Greenblum & Bernstein

[57] ABSTRACT

A device for combined spinal-epidural anesthesia, including an epidural needle having a bent free end portion with an inclined, pointed tip, and a hub fixedly connected to its other end and a tubular guide needle for a spinal needle. The guide needle has two inclined tips and is fixedly attached along at least part of its length to at least a portion of the straight section of the epidural needle. The guide needle is substantially shorter than the epidural needle and extends between a point located behind the bent free end portion of the epidural needle and a point located ahead of the hub thereof.

5 Claims, 1 Drawing Sheet

DEVICE FOR COMBINED SPINAL AND EPIDURAL ANESTHESIA

The present invention relates to a device for combined spinal and epidural anesthesia.

The advantages of combined spinal-epidural anesthesia, namely, a combination of the rapid response, reliable surgical anesthesia and extensive muscular relaxation produced by the spinal block, and the flexibility in duration of the epidural block which is easily prolonged to provide also postoperative analgesia, have been recognized for several years, yet the somewhat cumbersome procedure, largely due to the nonavailability, so far, of satisfactory applicators especially designed for this combined block, has been an obstacle to a more extensive acceptance of this promising technique.

Evans (U.K. application 2,124,503A-published Feb. 22, 1984), has disclosed an instrument for epidural and spinal anesthesia, which provides a spinal needle SN (FIG. 1) inside, and co-axial with, an epidural needle EN. The serious disadvantage of this device is the vulnerability of the point P of the spinal needle SN which is introduced into the epidural needle after the latter has entered the epidural space. As the terminal portion of the epidural needle EN is bent (as practically all epidural needles are), it is clear that, in order to move past this terminal portion, the spinal needle SN must flex. The force required for this relatively sudden flexure is transmitted via the fine point P of the spinal needle as soon as it "hits" the interior wall of the bent portion of the epidural needle EN. This forceful encounter is very much liable to break or at least dull the point P of the spinal needle, thereby increasing patient trauma and the likelihood of complications.

It is one of the objects of the present invention to overcome the limitations and drawbacks of prior-art applicators for combined spinal and epidural anesthesia, and to provide a device that considerably simplifies the procedure without entailing the risk of damage to the point of the spinal needle with the above-mentioned associated hazards, and that facilitates the use of relatively thin spinal needles which significantly reduce the incidence and severity of post-spinal headaches.

According to the invention this is achieved by providing an epidural needle having a bent free end portion with an inclined, pointed tip, and a hub fixedly connected to its other end, and a tubular guide needle for a spinal needle, said guide needle having two inclined tips and being fixedly attached along at least part of its length to at least a portion of the straight section of said epidural needle, said guide needle being substantially shorter than said epidural needle and extending between a point located behind said bent free end portion of said epidural needle and a point located ahead of the hub thereof.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
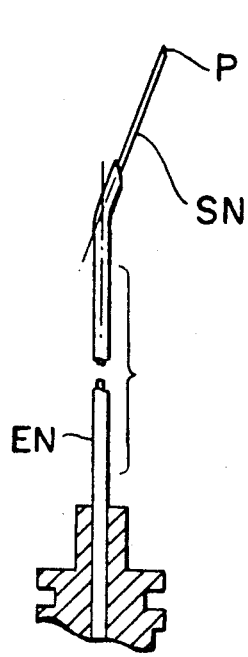
FIG. 1 represents a prior-art device.
Figure 2:
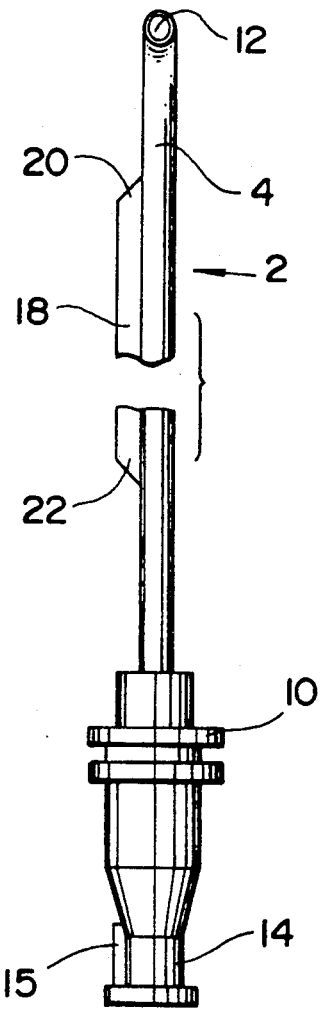
FIG. 2 represents the device according to the invention, with the obturator in position.

Referring now to the drawings, there is seen in FIG. 2 an epidural needle 2 of the per se known type, having a straight shank 4, a bent terminal portion 6, an inclined, pointed tip 8 and a hub 10. Also seen is the tip 12 and the hub 14 of the plastic obturator associated with the epidural needle 2. The key 15 of the obturator hub 14 and an appropriate keyway (not shown) in the hub 10 of the needle 2 ensure proper orientation of the end face 16 of the obturator relative to the inclined tip 8 of the needle 2.

Figure 3:
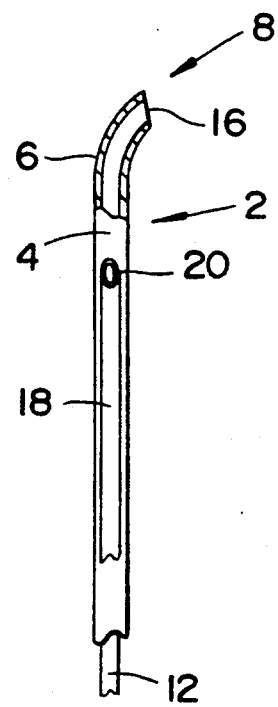
FIG. 3 is a partial view, in direction of arrow A in FIG. 1, of the device.

Further seen is a guide needle 18 of somewhat smaller diameter and substantially lesser length than the epidural needle 2, fixedly attached to the latter, preferably by bracing with a silver alloy. As can be seen in FIGS. 2 and 3, the guide needle has two inclined tips 20 and 22, and extends between a point located behind the bent terminal portion 6 of the epidural needle 2 and a point located ahead of the hub 10. The guide needle 18 is located in a plane normal to the plane defined by the bent terminal portion 6 of the epidural needle 2 and its shank portion 4.

The spatial relation between the epidural needle 2 and the guide needle 18 is clearly seen in FIG. 3.

Figure 4:
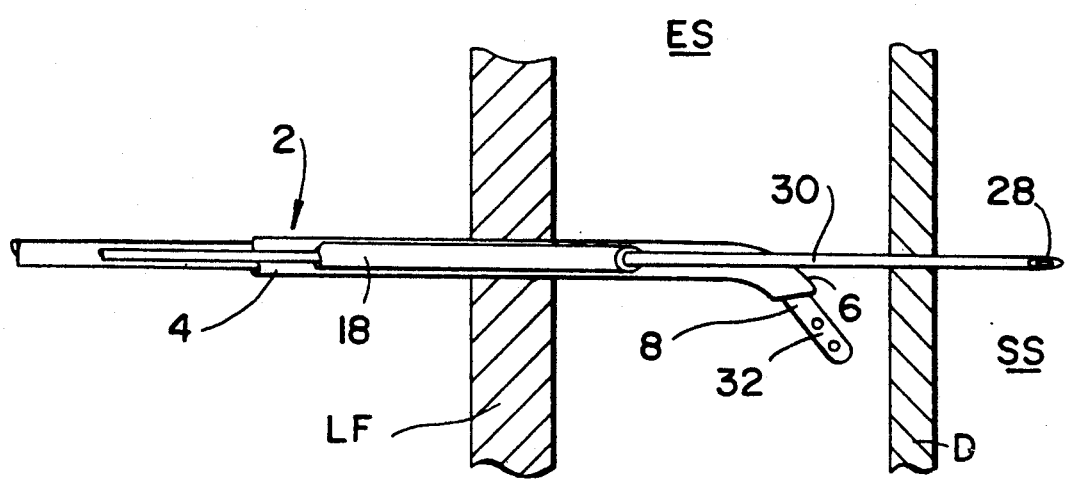
FIG. 4 is an enlarged view, showing the device after penetration, into the epidural space, of the epidural needle and catheter, and, into the spinal space, of the spinal needle.

FIG. 4 is an enlarged view of the distal part of the device, after puncture, by the tip 8 of the epidural needle 2, of the schematically indicated ligamentum flavum LF, which puncture leaves the epidural needle in the epidural space ES, and the subsequent penetration, by the tip 28 of a relatively thin spinal needle 30, of the dura D and its entrance into the spinal (subarachnoid) space SS. The spinal needle slidingly fits the guide needle 18 and is long enough, to project beyond the point of the epidural-needle tip 8 by 8–10 mm, so that the tip 28 of the spinal needle 30 is already in the spinal space SS, while the tip 8 of the epidural needle 2 remains in the epidural space ES.

Also shown is the epidural catheter 32 through which an epidural anesthetic is eventually introduced into the epidural space ES.

The procedure is quite simple and straightforward: First, the spinal needle 30 is introduced into the guide needle 18 as far as the distal end of the latter. Then, the now combined spinal-epidural needle (CSEN) is introduced into the selected intervertebral space and the epidural space ES is located, using the well-known indicator methods. After that, the spinal needle is slowly pushed in to puncture the dura D, until cerebrospinal fluid is obtained. Then (the obturator 12 having been removed first), the epidural catheter 32 is introduced into the epidural space, and the anesthetic is injected through the spinal needle into the spinal space. Subsequently, the spinal needle 30 is slowly withdrawn from the guide needle 18 and then the CSEN is withdrawn, leaving the epidural catheter 32 in position in the epidural space ES.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for combined spinal-epidural anesthesia, comprising:

an epidural needle having a straight section terminating in a bent free end portion with an inclined, pointed tip, and a hub fixedly connected to the other end of the epidural needle, and a tubular needle guide for slidably receiving a spinal needle, said needle guide having two inclined tips and being fixedly attached along at least part of its length to at least a portion of the straight section of said epidural needle on the outside thereof, said needle guide being substantially shorter than said epidural needle and extending between a point located behind said bent free end portion of said epidural needle and a point located ahead of the hub thereof.

2. The device as claimed in claim 1, wherein said needle guide is located in a plane substantially normal to the plane defined by said epidural needle and its bent free end portion.

3. The device as claimed in claim 1, further comprising a spinal needle slidingly fitting said needle guide and being of sufficient length to linearly project from the front tip of said needle guide for a distance far enough to penetrate the dura mater and enter the subarachnoid space, while the tip of said epidural needle remains in the epidural space.

4. The device as claimed in claim 1, further comprising obturators for said epidural needle and said spinal needle.

5. A device for combined spinal-epidural anesthesia comprising:

a) a tubular epidural needle having a bent terminal portion defining a forward inclined tip for insertion into the epidural space between the ligamentum flavum and dura mater of a patient; and b) a tubular needle guide attached to the exterior of the epidural needle, said guide having an inclined tip located at a position rearwardly spaced from the inclined tip of said epidural needle;

c) said device including a spinal needle slidably received in said needle guide and having a pointed tip and a length that causes the pointed tip of said spinal needle to project forwardly beyond the inclined tip of said epidural needle and effect penetration of the dura mater and enter the spinal space of the patient when the spinal needle slides in said guide.

* * * * *